(12) United States Patent
Kim et al.

(10) Patent No.: US 6,368,583 B1
(45) Date of Patent: Apr. 9, 2002

(54) HAIR TREATMENT COMPOSITION

(75) Inventors: Son Nguyen Kim, Hemsbach; Karin Sperling, Neustadt, both of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/068,007

(22) PCT Filed: Nov. 6, 1996

(86) PCT No.: PCT/EP96/04857

§ 371 Date: Apr. 29, 1998

§ 102(e) Date: Apr. 29, 1998

(87) PCT Pub. No.: WO97/17052

PCT Pub. Date: May 15, 1997

(30) Foreign Application Priority Data

Nov. 6, 1995 (DE) .......................................... 195 41 329

(51) Int. Cl.[7] .................................................. A61K 7/11
(52) U.S. Cl. ............................... 424/70.122; 424/70.1; 424/70.11; 424/70.12
(58) Field of Search ........................... 424/70.1, 70.122, 424/70.11

(56) References Cited

U.S. PATENT DOCUMENTS

| | | | |
|---|---|---|---|
| 3,412,054 A | 11/1968 | Milligan et al. | 260/18 |
| 3,523,998 A | 8/1970 | Feinstone et al. | 424/78 |
| 3,658,939 A | 4/1972 | Carpenter et al. | 260/858 |
| 3,734,874 A | 5/1973 | Kibler et al. | 260/29.2 |
| 4,150,216 A | 4/1979 | Quack et al. | 528/290 |
| 4,300,580 A | 11/1981 | O'Neill et al. | 132/7 |
| 4,521,404 A * | 6/1985 | Lorenz et al. | 526/264 |
| 4,743,673 A | 5/1988 | Johnston et al. | 528/60 |
| 4,833,225 A | 5/1989 | Schaefer et al. | 528/28 |
| 5,643,581 A | 7/1997 | Mougin et al. | 424/401 |
| 6,262,176 B1 * | 7/2001 | Kim et al. | |

FOREIGN PATENT DOCUMENTS

| | | |
|---|---|---|
| DE | 4304697 A1 * | 9/1994 |
| EP | 619 111 | 10/1994 |
| GB | 1128568 | 9/1968 |
| GB | 1318818 | 5/1973 |
| GB | 1499080 | 1/1978 |
| GB | 2188948 | 10/1987 |
| WO | 89/07118 | 8/1989 |
| WO | 9325179 * | 12/1993 |
| WO | 9523579 * | 8/1995 |

OTHER PUBLICATIONS

Derwent Abst. 94–272346/34 (DE 4304697; Feb. 16, 1993).
Derwent Abst. 95–329124/43 (DE 4408727; Mar. 15, 1994).
Derwent Abst. 94–249868/31 (DE 4241118; Dec. 7, 1992).
Derwent Abst. 94–043715/06 (DE 4225045; Jul. 29, 1992).

* cited by examiner

Primary Examiner—Thurman K. Page
Assistant Examiner—Brian K. Seidleck
(74) Attorney, Agent, or Firm—Keil & Weinkauf

(57) ABSTRACT

The present invention relates to hair treatment compositions comprising a hairsetting polymer together with a salt of the formula I

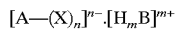

$$[A-(X)_n]^{n-}\cdot[H_mB]^{m+}$$

where A, X, B, n and m are as defined in the description. The novel hair treatment compositions possess improved ease of washing out, smoothness and transparency and can be formulated with a reduced VOC content.

16 Claims, No Drawings

HAIR TREATMENT COMPOSITION

This application is a 371 of PCT/EP96/04857, filed Nov. 6, 1996.

The present invention relates to hair treatment compositions and, in particular, to hairsetting compositions in the form of a hairspray.

Water soluble or water dispersible polymers, for example polyesters, polyamides or polyurethanes, are becoming increasingly important owing to their particularly low viscosity in water and in water/ethanol. For instance, water soluble polyurethanes which contain copolymerized carboxyl containing diols are known from U.S. Pat. Nos. 3,412,054 and 3,658,939. They are used as adhesives, as coating compositions and in printing inks. Polyurethanes containing sulfonate groups and/or carboxylate groups, which are dispersible in water, are known from DE-A-15 70 615. They are used, for example, for the coating and for the impregnation of textiles, leather, paper, wood and metals. Protective rights documents U.S. Pat. No. 4,300,580, U.S. Pat. No. 3,734,874, DE-A-26 33 418 and WO-A-89/07118 disclose polyesters which contain NaSO3 groups and whose main chain is synthesized by condensation reaction, and which can be broken down into shorter segments by hydrolysis of the ester groups.

It is also known that maleic anhydride and trimellitic anhydride can be used to prepare water soluble esters. The anhydride group provides carboxyl groups which, by neutralization with amines, metal hydroxides and metal carbonates, are converted to carboxylate groups, thereby obtaining solubility in water. From DE-A-26 37 167 and U.S. Pat. No. 3,523,998 it is known that polycarboxylic acids and their anhydrides, as well, may also contribute, as polymer components, to rendering polyesters soluble in water. A cosmetic application of such polymers, however, has not hitherto been described.

In cosmetology, film former polymers are used for setting, shaping and improving the structure of hair. The hair treatment compositions generally include a solution of the film former in an alcohol or in a mixture of alcohol and water.

U.S. Pat. No. 4,743,673 describes hydrophilic polyurethane polymers containing carboxyl groups in the polymer backbone. These polyurethanes are synthesized from a polyol component, which may be an alkylene glycol, a polyoxyalkylene glycol or a linear polyesterdiol, from a carboxylic ester component containing hydroxyl or amino groups, and from an organic isocyanate or isocyanate precursor. The polyurethane therefore contains, attached to the polymer backbone, ester groups which are subsequently hydrolyzed by heating under reflux for from 30 to 60 minutes with a strong base, such as sodium hydroxide or potassium hydroxide. The product obtained is no longer soluble either in water or in ethanol to give a clear solution. It is no longer soluble in water but is only soluble in lower aliphatic alcohols and other solvents. In particular when a polyesterdiol is used as polyol component, the treatment with the strong base under reflux conditions results in hydrolysis not only of the ester groups of the carboxylic ester component but also of the ester groups present in the polyurethane chain. There is therefore cleavage of the polyurethane chain and a drastic decrease in the molecular weight of the polyurethanes. Use of the polyurethanes in hairsprays is indeed mentioned; however, in practice the films obtained with these polyurethanes are unusable for hair cosmetology, since they are either insoluble in water or possess too low a molecular weight and therefore an inadequate setting effect.

DE-A-42 25 045 describes the use of water-soluble or water-dispersible anionic polyurethanes as hairsetting agents. These polyurethanes are synthesized from
a) at least one compound containing two or more active hydrogen atoms per molecule,
b) at least one diol which contains acid groups or salt groups, and
c) at least one diisocyanate.

They possess a glass transition temperature of at least 15° C. and acid numbers from 12 to 150. As component a), polyethylene glycol, neopentylglycol and polyesterols are preferably employed. Preferred components (b) are dimethylolpropanoic acid, a condensation product of pyromellitic dianhydride and neopentylglycol, and a condensation product of 5-sodium-sulfonatoisophthalic acid with neopentylglycol.

DE-A-42 41 118 describes the use of cationic polyurethanes and polyureas as auxiliaries in cosmetic and pharmaceutical formulations. They are employed in particular as film formers in hair-setting compositions, and are synthesized from
a) at least one diisocyanate which may have already been reacted beforehand with one or more compounds containing two or more active hydrogen atoms per molecule, and
b) at least one diol, primary or secondary amino alcohol, primary or secondary diamine or primary or secondary triamine having one or more tertiary, quaternary or protonated tertiary amine nitrogen atoms.

The polymers possess a glass transition temperature of at least 25° C. and an amine number of 50 to 200, based on the nonquaternized or protonated compounds.

EP-A-619 111 describes the use of polyurethanes containing carboxylate groups in hairsetting compositions. As a compound which provides the carboxylate groups, these polyurethanes include a compound of the formula

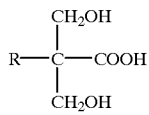

where R is hydrogen or $C_1$–$C_{20}$ alkyl. At least some of the carboxylic acid groups in this case are neutralized with an organic or inorganic base in order to provide the number of carboxylate groups necessary to render the polyurethane soluble in water or in a mixture of water and a polar organic solvent.

EP-A-636 361 discloses cosmetic compositions comprising a film-forming polymer with at least one polysiloxane moiety and at least one polyurethane and/or polyurea moiety which contains anionic or cationic groups. Because of the siloxane moiety, the films are smoother, result in better grip and the hair becomes smoother in comparison to nonsiloxane-containing polymers. In analogy to the mentioned polyurethanes, the ease of washing out of these siloxane-containing film formers is not satisfying either, if the K value >24. However, if the K value is lower than 24, the ease of washing out is acceptable, but the fixing effect is insufficient.

It is further known to add a silicone compound (frequently polydimethylsiloxane; CTFA name: Dimethicon, e. g. Abil 10–100 000, Goldschmidt Company) during the formulation of hair treatment compositions, for example of hair spray. Due to the distinct hydrophobic character of the products, they have a positive effect on the film characteristics of the hair treatment composition. However, due to being highly hydrophobic, the polysiloxanes are very poorly soluble in water as well as ethanol. Phase separation from an ether water solution results in the film being turbid and unevenly distributed. Thus the hair is poorly leachable and an insoluble silicone residue remains on the hair, i. e. the hair is heavy and "greasy".

Hairsetting compositions are generally sprayed onto the hair in the form of aqueous alcoholic solutions. After the evaporation of the solvent, the hair is held in the desired shape at the points of mutual contact of the polymer which remains. The polymers should on the one hand be sufficiently hydrophilic that they can be washed out of the hair but on the other hand should be hydrophobic, so that the polymer-treated hair retains its shape, even in the case of high atmospheric humidity, and there is no sticking together of individual hairs. In order to obtain a hairsetting effect of maximum efficiency, it is additionally desirable to employ polymers which possess a relatively high molecular weight (K value >25) and a relatively high glass transition temperature (at least 15° C.). Polymers which meet these requirements, however, are more difficult to wash out owing to the relatively high molecular weight.

Another factor to be taken into account when formulating hairsetting compositions is that a reduction in the content of alcohol and propellant is necessary owing to the environmental provisions for controlling the emission of volatile organic compounds (VOCs) into the atmosphere.

The polymers described in the abovementioned publications go only part of the way to meeting these mutually contradictory requirements. Thus, the polymers described in DE-A-42 25 045 and 42 41 118 and in EP-A-619 111 on the one hand possess the desired setting effect owing to their high molecular weight. On the other hand, however, they cannot be washed out sufficiently. The polymers described in U.S. Pat. No. 4,743,673, owing to their low molecular weight brought about by hydrolysis of the ester groups, do not possess the necessary setting effect.

It is an object of the present invention, therefore, to provide hair treatment compositions which on the one hand can be used as hairsetting compositions but on the other hand also possess improved ease of washout (redispersibility).

We have found that this object is achieved, surprisingly, if the polymers which can be used as hairsetting agents are employed together with a salt, which is soluble in water or in an water/alcohol mixture, of an organic acid and an amine.

The present invention therefore provides a hair treatment composition comprising:

A) at least one hairsetting polymer which is dispersible or soluble in water or in a mixture of water and a $C_1$–$C_4$ alcohol, and B) at least one salt which is dispersible or soluble in water or in a mixture of water and a $C_1$–$C_4$ alcohol and has the formula

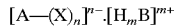

where A is a cosmetically acceptable, aliphatic, cycloaliphatic or aromatic radical which can have 1, 2 or 3 substituents which may be identical or different and are selected from $C_1$–$C_6$ alkyl, $C_1$–$C_6$ alkoxy, mono or polyhydroxy $C_1$–$C_6$ alkyl, hydroxyl and amino, it being possible for the chain of the aliphatic radical to be interrupted by up to 30 —CONH groups and for the ring of the cycloaliphatic radical to have a —CO—N group, with two cycloaliphatic radicals being attached in each case to the nitrogen atom by way of a $C_2$–$C_8$ alkylene or p-xylylene group;

X is a carboxylate, sulfonate, phosphate or phosphonate group;

B is a cosmetically acceptable amine base;

n is 1 to 30, preferably 1 to 20 and especially 1 to 6; and m is the valency of the amine B.

The following acids are preferably employed to form the salt:

1. Aromatic carboxylic acids, especially benzenecarboxylic acids, which have 1, 2, 3 or 4 carboxyl groups and which may or may not carry one, two or three hydroxyl or sodium sulfonate groups. Examples of these are:

benzoic acid, 1,2-, 1,3- or 1,4-benzenedicarboxylic acid (phthalic acid, isophthalic acid or terephthalic acid), 1,2,4- or 1,3,5-benzenetricarboxylic acid, 1,2,4,5- or 1,3,4,5-benzenetetracarboxylic acid;

2-hydroxybenzoic acid, 3-hydroxybenzoic acid, 4-hydroxybenzoic acid, 2,3- or 2,4-dihydroxybenzoic acid or 5-hydroxyisophthalic acid;

5-sulfobenzene 1,3-icarboxylic acid (5-$SO_3$H-isophthalic acid);

benzenesulfonic acid, 1,2-, 1,3- or 1,4-benzenedisulfonic acid or 1,2,4- or 1,3,5-benzenetrisulfonic acid;

2-hydroxybenzenesulfonic acid, 3-hydroxybenzenesulfonic acid or 4-hydroxybenzenesulfonic acid.

2. Aliphatic carboxylic acids having 1 to 12, in particular 1 to 6 carbon atoms, which carry 1 to 6 and, in particular, one, two, three or four carboxyl groups and, if desired, one, two, or three and up to six hydroxyl groups. Examples of these are:

1,2,3,4-butyltetracarboxylic acid;

lactic acid, tartaric acid, citric acid, malic acid, gluconic acid or glyoxylic acid;

oligoaminocarboxylic acids of the formula III

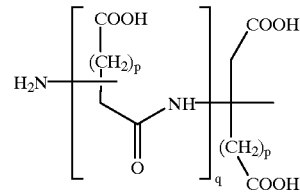

(II)

where p is 1, 2 or 3 and q is 0 to 30, preferably 0 to 20.

3. Cycloaliphatic carboxylic acids having 1, 2, 3 or 4 carboxyl groups and, if desired, one or two hydroxyl groups. Examples of these are:

1,2-, 1,3- and 1,4-cyclohexanedicarboxylic acid, 1,2,3,4-cyclopentanetetracarboxylic acid;

1,2,3,6-tetrahydrophthalic acid;

amide containing carboxylic acids of the formula

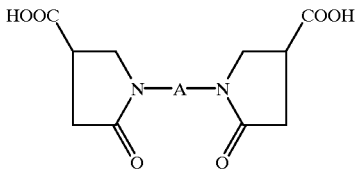
(III)

4. Siloxane-containing acids. Preferred are 4.1 monobasic siloxane-containing acids of the formula $$R^1\text{—NHCO—}R^2\text{—COOH} \quad (IV)$$

where $R^1$ represents

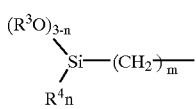

with n=0–3
and m=1–6,
where $R^3$ and $R^4$ represent $C_1$–$C_6$ alkyl and n represents 1 to 6 and $R^2$ represents one of the following groups

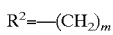

with m=2–6, especially 2 and 3,

—CH=CH—

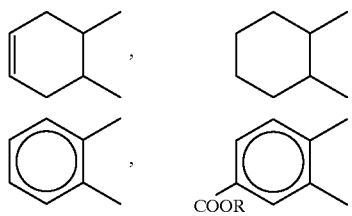

or of the formula

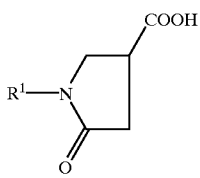
(V)

where $R^1$ is as defined above.
Examples of the compounds of formulae IV and V are:

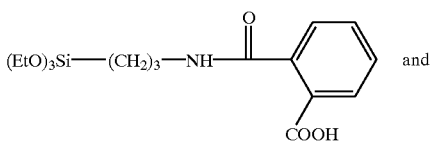
and

The carboxylic acids of formula IV can be obtained by reacting a monobasic siloxane-containing amine of the formula $R^1$—$NH_2$
with the corresponding anhydride

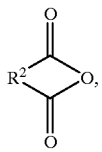

where $R^1$ and $R^2$ are as defined above.

The compounds of formula V can be obtained by condensing an amine $R^1NH_2$ ($R^1$ as defined above) with itaconic acid.

4.2 Dibasic, siloxane-containing acids of the formula:

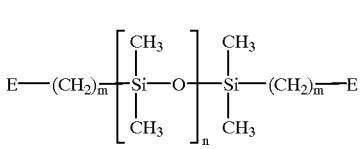
(VI)

where E represents COOH or

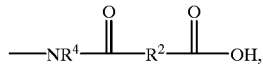

where $R^2$ is as defined above and $R^4$ represents H or $C_1$–$C_6$ alkyl; m is 1 to 6 and n is 1 to 50. If E is COOH, n is preferably 1 to 10
and if E is

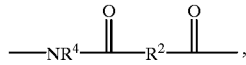

n is preferably 5 to 35.
Examples of carboxylic acids of the formula VI are:

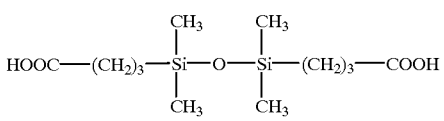

of Gelect Co. and the Tegomer C—Si-types, e. g. C—Si 2142 and C—Si 2342 of Goldschmidt Co.; or
dibasic, siloxane-containing acids of the formula

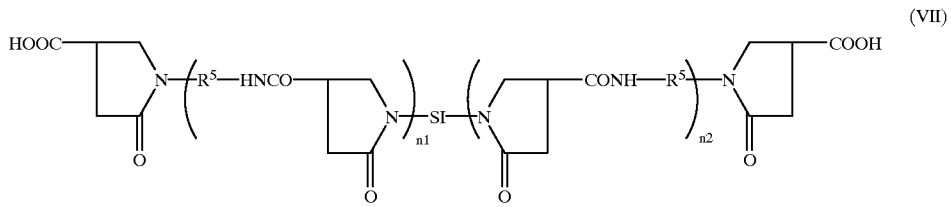

wherein $R^5$ represents $C_2$–$C_4$ alkylene and n1+n2=0–20, preferably=0, and SI represents

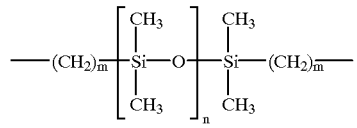

wherein m is 1 to 6 and n is 1 to 10.

Carboxylic acids of formula VII, wherein n1+n2=0, are obtained by condensing itaconic acid with the corresponding diamine in a molar ratio of 2:1. If n1+n2≠0, first itaconic acid and the siloxane-containing diamine are reacted and afterwards the obtained condensation product is reacted with a siloxane-free diamine in the particular corresponding molar ratios. For example, if n1+n2=5, 7 moles of itaconic acid are reacted with 1 mole of siloxane-containing diamine, and afterwards with 5 moles of siloxane-free diamine, e. g. with ethylene diamine. Generally the condensation with the siloxane-free diamine is carried out at 150–170° C.

4.3 polybasic, siloxane-containing acids of the formula:

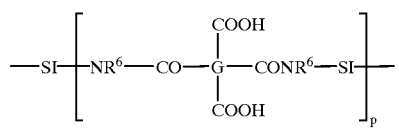

wherein $R^6$ represents H or $C_1$–$C_6$ alkyl, SI is as defined above, p represents 1 to 100 and G represents the tetravalent residue of a dianhydride

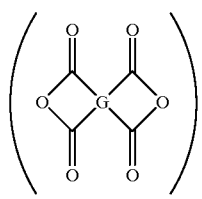

of the formula:

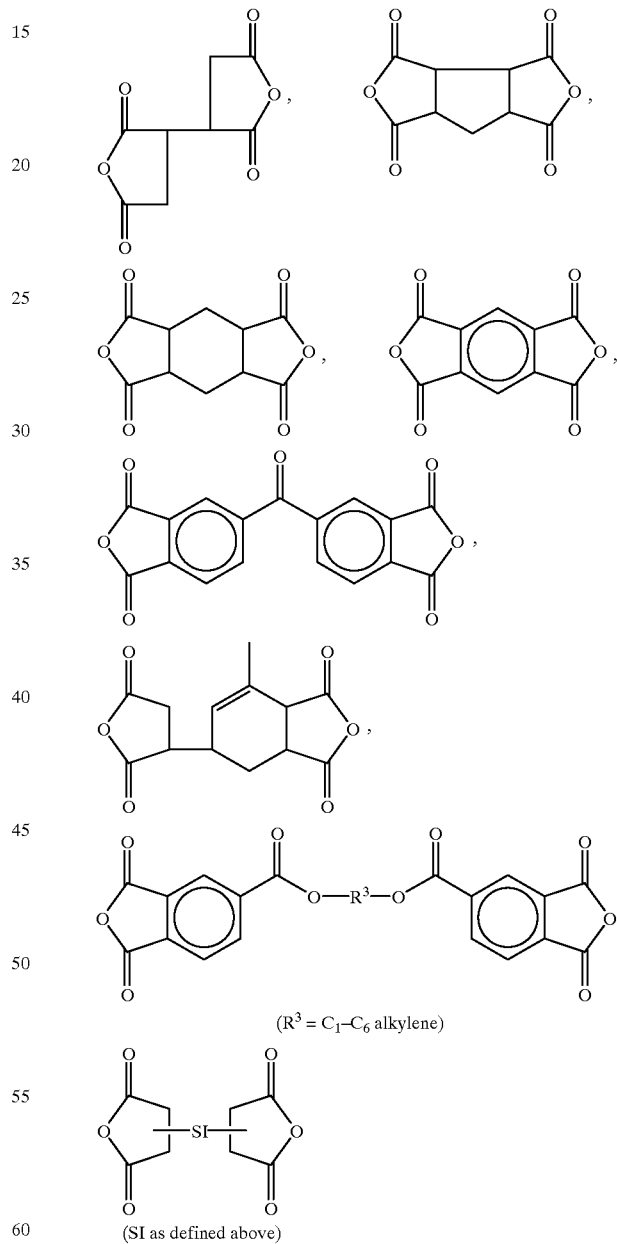

The compounds of formula VIII can be obtained by reacting a polysiloxane-containing diamine $HR^6N$—SI—$NR^6H$ with one of the dianhydrides in a solvent or without a solvent at a temperature in the range from 20 to 120° C. Up to 80 mol % of the polysiloxane-containing diamine can be replaced by a polyamide diamine. The molar ratio of dianhydride to diamine is in the range from 0.5 to 2.

The products analogous to VIII can be obtained by reacting a polysiloxane-containing dianhydride of the structure

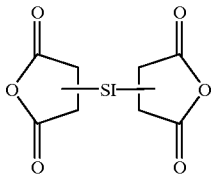

(SI as defined above) with a diamine.

4.4 polybasic, siloxane-containing acids which are polycondensates, the chains of which are formed from at least one polysiloxane moiety and at least one polyurethane moiety and/or polyurea moiety, wherein the polyurethane and/or polyurea moieties comprise carboxylic and/or sulfonic groups. Particularly concerned are those polyurethanes or polyureas which are made of a diisocycanate and a diol or a diamine, where the molar ratio of NCO/acidic hydrogen atoms is <0.9 or >1.1. The K value of the polymers (determined as 0.1% solution in N-methyl pyrrolidone) is preferably <24. Such polycondensates are described in EP-A-636 361 to which reference is made herewith.

Preferred are the polycondensates with polysiloxane moieties of the formula

 (IX)

where E represents O or NH, $R^7$ represents a $C_1$–$C_6$ alkylene or phenylene and SI is as defined above, and with polyurethane and/or polyurea moieties of the formula

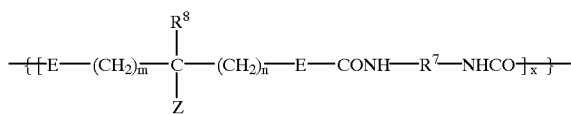

where E represents O or NH, $R^7$ represents $C_1$–$C_6$ alkylene or phenylene, $R^8$ represents H or $C_1$–$C_4$ alkyl, Z represents COOH or $SO_3H$, m and n independently are 1 to 6 and x is 1 to 10.

Amines which can be employed are all cosmetically acceptable amines which form salts with the above acids. Preference is given to aliphatic monoamines or polyamines, especially alkylamines, $C_2$–$C_8$ alkylenediamines and triamines, the alkyl groups independently of one another preferably having 1 to 12 and, in particular, 1 to 6 carbon atoms and, if desired, 1 to 6 hydroxyl groups. Amines containing hydroxyl groups can be used in particular. Examples of appropriate amines are monoethanolamine, diethanolamine, triethanolamine, dimethylethanolamine, diethylethanolamine, methyldiethanolamine, ethyldiethanolamine, butyldiethanolamine, 2-amino-2-methylpropanol, 2-amino-2-methylolpropanol and polyamies, such as N-methyldipropylenetriamine or N-methylglucamine.

Preferred siloxane-containing amines are:

monovalent, siloxane-containing amines of the formula

wherein $R^1$ has the meaning mentioned in connection with the compounds of formula IV and $R^9$ and $R^{10}$ independently represent H, $C_1$–$C_6$ alkyl or $C_1$–$C_6$ hydroxyalkyl. Examples of such amines are those of the formulae

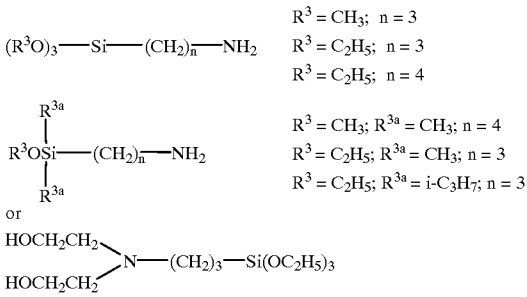

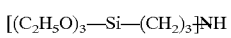

Such amines can be obtained commercially (Hüls Co.).

bivalent, siloxane-containing amines of formula VI, where E represents $NH_2$ or $NHC_1$–$C_6$ alkyl. Examples of such amines are the Tegomer A-Si-types of the Goldschmidt Co.

polyvalent, siloxane-containing amines which are polycondensates, the chains of which are formed by at least one polysiloxane moiety and at least one polyurethane and/or polyurea moiety, wherein said polyurethane and/or polyurea moieties contain amine groups. EP-A-636 361 describes such polycondensates to which reference is made herewith.

Preferred polycondensates with polysiloxane moieties are those of the formula

 (IX)

where E is O or NH, $R^7$ is a $C_1$–$C_6$ alkylene or phenylene and SI is as defined above, and with polyurethane and/or polyurea moieties of the formula

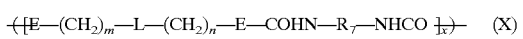 (X)

where E is O or NH,

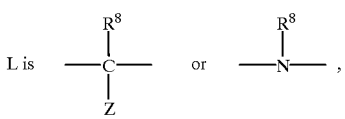

$R^7$ is $C_1$–$C_6$ alkylene or phenylene, $R^8$ is H or $C_1$–$C_4$ alkyl, Z is $NR^{11}R^{12}$, m and n are independently 1 to 6, x is 1 to 10 and $R^{11}$ and $R^{12}$ are independently $C_1$–$C_6$ alkyl.

The molecular weight of a siloxane-free salt is preferably less than 3000 and in particular less than 2000. The molecular weight of siloxane-containing salts can be up to 30 000.

Particularly preferred are the salts of isophthalic acid, 5-$NaSO_3$-isophthalic acid, trimellithic acid or 1,3,5-benzenetricarboxylic acid with 2-amino-2-methylpropanol as well as siloxane-containing salts of which the following types are preferred:

a) the salts of a monobasic acid with a monovalent amine, where at least one of the components contains a siloxane group;

b) the salts of a monobasic acid with a polyvalent amine, where at least one of the components contains a siloxane group;

c) the salts of a polybasic acid with a monovalent amine, where at least one of the components contains a siloxane group;

d) the salts of a dibasic acid with a divalent amine, where at least one of the components contains a siloxane group;

In a preferred embodiment of the invention the composition together with a siloxane-containing salt contains at least one silicone, preferably in an amount from 0.0001 to 0.2% by weight, based on the overall weight of the composition.

Particularly preferred is a composition which contains:

A) 0.5 to 15% by weight of a siloxane-free hairsetting polymer,

B) 0.1 to 8% by weight of a polysiloxane-containing salt and

C) 0.0005 to 0.15% by weight, especially 0.001 to 0.1% by weight of silicone.

Hairsetting polymers which can be used in particular are polyurethanes, polyesters, polyamides, poly(amide)esters, homopolymers and copolymers of monoolefinically unsaturated monomers, these polymers having ionogenic and/or ionic groups attached to the polymer chain so that the polymers are dispersible or soluble in water. These groups are preferably carboxyl groups and/or sulfonic acid groups and/or nitrogen containing groups (amines) or carboxylate groups and/or sulfonate groups and/or quaternized nitrogen containing groups. Examples of such polymers are described in U.S. Pat. Nos. 3,475,206 and 3,412,054 and in DE-A-15 70 615. It is preferred, however, to use the polymers described in DE-A-42 25 045, DE-A-42 41 118 and EP-A-619 111 and those described in DE-A-42 24 761. These are the following polymers:

1. Water soluble or dispersible anionic polyurethanes comprising
   a) at least one compound containing two or more active hydrogen atoms per molecule,
   b) at least one diol which contains acid groups or salt groups, and
   c) at least one diisocyanate, and possessing a glass transition temperature of at least 15° C. and acid numbers in the range from 12 to 150, preferably from 30 to 90, and the salts thereof.

Component a) comprises, in particular, diols, amino alcohols, diamines, polyesterols, polyetherols having a number average molecular weight of in each case up to 3000 or mixtures thereof, it being possible for up to 3 mol % of said compounds to be replaced by triols or triamines. Diols and polyesterdiols are preferred. In particular, component (a) comprises at least 50% by weight, based on the overall weight of component (a), of a polyesterdiol.

Suitable polyesterdiols are all those which are commonly employed for preparing polyurethanes, especially reaction products of phthalic and diethylene glycol, isophthalic acid and 1,4-butanediol, isophthalic acid/adipic acid and 1,6-hexanediol, and adipic acid and ethylene glycol or 5-NaSO$_3$-isophthalic acid, phthalic acid, adipic acid and 1,6-hexanediol.

Examples of diols which can be used are ethylene glycol, propylene glycol, butylene glycol, neopentylglycol, polyetherols, such as polyethylene glycols having molecular weights of up to 3000, block copolymers of ethylene oxide and propylene oxide having number average molecular weights of up to 3000, or block copolymers of ethylene oxide, propylene oxide and butylene oxide which contain the alkylene oxide units copolymerized in random distribution or in the form of blocks. Ethylene glycol, neopentylglycol, di-, tri-, tetra-, penta- or hexaethylene glycol are preferred. Other diols which can be used are poly(α-hydroxycarboxylic acid)diols.

Examples of suitable amino alcohols are 2 aminoethanol, 2-(n-methylamino)ethanol, 3-aminopropanol or 4-aminobutanol.

Examples of suitable diamines are ethylenediamine, propylenediamine, 1,4-diaminobutane and 1,6-diaminohexane and also α,ω-diamines which can be prepared by aminating polyalkylene oxides with ammonia.

Component b) comprises, in particular, dimethylolpropanoic acid or compounds of the formulae

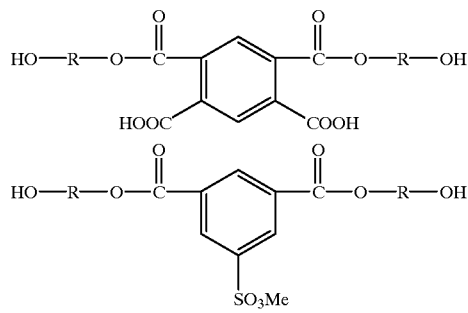

where each R is C$_2$–C$_{18}$ alkylene and Me is Na or K.

Component c) comprises, in particular, hexamethylene diisocyanate, isophorone diisocyanate, methyldiphenyl isocyanate (MDI) and/or tolylene diisocyanate.

The polyurethanes are obtainable by reacting the compounds of groups a) and b) with the compounds of group c) at from 70 to 130° C. in an inert solvent and under an inert gas atmosphere. This reaction can if desired be carried out in the presence of chain extenders in order to prepare polyurethanes of relatively high molecular weights. As is customary in the preparation of polyurethanes, components [(a)+(b)]:(c) are employed in a molar ratio of 0.8 to 1.1:1. The acid number of the polyurethanes is determined by the composition and concentration of the compounds of component (b) in the mixture of components (a)+(b). The polyurethanes have H. Fikentscher K values (determined in 0.1% strength by weight solutions in N-methylpyrrolidone at 25° C. and pH 7) of 15 to 100, preferably 25 to 50.

The polyurethanes containing acid groups are soluble in water following neutralization (partial or complete) or can be dispersed without the aid of emulsifiers. In general, the salts of the polyurethanes have a better solubility in water or dispersibility in water than the nonneutralized polyurethanes. As a base for the neutralization of polyurethanes, it is possible to use alkali metal bases such as sodium hydroxide, potassium hydroxide, sodium carbonate, sodium hydrogen carbonate, potassium carbonate or potassium hydrogen carbonate and alkaline earth metal bases such as calcium hydroxide, calcium oxide, magnesium hydroxide or magnesium carbonate, and also ammonia and amines. To neutralize the polyurethanes which contain acid groups it has proven particularly appropriate to use 2-amino-2-methylpropanol, diethylaminopropylamine and triisopropanolamine. The polyurethanes containing acid groups can also be neutralized with the aid of mixtures of two or more bases, for example mixtures of sodium hydroxide and triisopropanolamine. Depending on the intended application, neutralization may be carried out partially, for example to the extent of 20 to 40%, or completely, ie. to the extent of 100%.

These polymers and their preparation are described in more detail in DE-A-42 25 045, to which in its entirety reference is hereby made.

2. Water soluble or dispersible cationic polyurethanes and polyureas comprising
    a) at least one diisocyanate which may have already been reacted beforehand with one or more compounds containing two or more active hydrogen atoms per molecule, and
    b) at least one diol, primary or secondary amino alcohol, primary or secondary diamine or primary or secondary triamine having one or more tertiary, quaternary or protonated tertiary amine nitrogen atoms, which have a glass transition temperature of at least 25° C. and an amine number of from 50 to 200, based on the nonquaternized or protonated compounds, and the salts thereof. The amine number is preferably in the range 65 to 180, especially 70 to 170, particularly preferably 75 to 160, very particular preferably, 80 to 150.

Preferred diisocyanates are as indicated above under 1). Compounds having two or more active hydrogen atoms are diols, amino alcohols, diamines, polyesterols, polyamide diamines and polyetherols. Suitable compounds of this kind are as indicated above under 1).

The polyurethanes are prepared as indicated above under 1). Charged cationic groups can be produced in the polyureas from the tertiary amine nitrogen atoms present either by protonation, for example with carboxylic acids such as lactic acid, or by quaternization, for example with alkylating agents such as $C_1$–$C_4$-alkyl halides or $C_1$–$C_4$-alkyl sulfates. Examples of such alkylating agents are ethyl chloride, ethyl bromide, methyl chloride, methyl bromide, dimethyl sulfate and diethyl sulfate.

These polymers and their preparation are described in more detail in DE-A-42 41 118, to which in its entirety reference is hereby made.

3. Linear polyurethanes containing carboxylate groups, comprising
    a) a 2,2-hydroxymethyl-substituted carboxylic acid of the formula

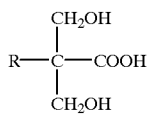

where R is hydrogen or $C_1$–$C_{20}$-alkyl, which is used in a quantity sufficient for from 0.35 to 2.25 milliequivalents of carboxyl groups to be present in the polyurethane per g of polyurethane,
    b) from 10 to 90% by weight, based on the weight of the polyurethane, of one or more organic compounds having not more than two active hydrogen atoms, and
    c) one or more organic diisocyanates.

Finally, the carboxyl groups present in the polyurethane are neutralized at least in part using an appropriate base. These polymers and their preparation are described in EP-A-619 111, to which in its entirety reference is hereby made.

4. Carboxyl containing polycondensation products having glass transition temperatures of >20° C. comprising anhydrides of tri- or tetracarboxylic acids and diols, diamines or amino alcohols (polyesters, polyamides or polyester amides). These polymers and their preparation are described in more detail in DE-A-42 24 761, to which in its entirety reference is hereby made.

5. Polyacrylates and polymethacrylates as described in more detail in DE-A-43 14 305, 36 27 970 and 29 17 504. Reference is hereby made to these publications in their entirety.

Further suitable hairsetting polymers are:

non ionic, water-soluble and water dispersable polymers or oligomers respectively, like polyvinylcaprolactam, e. g. Luviskol Plus (BASF) or polyvinylpyrrolidon and the copolymers thereof, especially with vinyl esters, like vinyl acetate, e. g. Luviskol VA 37 (BASF); polyamides, e. g. based on itaconic acid and aliphatic diamines;

amphoteric or zwitterionic polymers, like the octylacryl amide/methyl methacrylate/t-butylaminoethyl methacrylate/2-hydroxypropyl methacrylate copolymers obtainable under the name Amphomer® (Delft National) as well as zwitterionic polymers which are, for example, disclosed in the German applications DE 39 29 973, DE 21 50 557, DE 28 17 369 and DE 37 08 451. Acrylamidopropyltrimethylammonium chloride/acrylic acid or methacrylic acid copolymerisates respectively and the alkali and ammonium salts thereof are preferred zwitterionic polymers. Further suitable zwitterionic polymers are methacroylethylbetain/methacrylate copolymers which are commercially obtainable under the name Amersette® (AMERCHOL).

anionic polymers, like vinyl acetate/crotonic acid copolymers, such as those which are commercially obtainable under the names Resyn® (NATIONAL STARCH), Luviset® (BASF) and Gafset® (GAF), vinylpyrrolidone/vinyl acrylate copolymers, which for example can be obtained under the name of Luviflex® (BASF). A preferred polymer is vinyl pyrrolidone/acrylate terpolymer obtainable as Luviflex® VBM-35 (BASF), acrylic acid/ethyl acrylate/N-t-butylacryl amide terpolymers, which are sold for example under the name Ultrahold® strong (BASF); and Luvimer® (BASF, terpolymer of t-butyl acrylate/ethyl acrylate and methacrylic acid) or cationic (quaternised) polymers, e. g. Luviquat® (copolymer produced of vinyl pyrrolidone and vinylimidazoliummethochloride), Luviquat® Hold (copolymerisate produced of quaternised N-vinylimidazol, N-vinyl pyrrolidone and N-vinylcaprolactam), Merquat® (polymer based on dimethyldiallylammoniumchloride), Gafquat® (quaternary polymers, resulting from reacting polyvinyl pyrrolidone with quaternary ammonium compounds), Polymer JR (hydroxyethylcellulose with cationic groups), Polyquaternium types (CTFA names) etc.

The polymers employed in accordance with the invention preferably have a K value of 25 to 100, preferably 25 to 50. The polymers are present in the novel composition in general in a quantity in the range from 0.2 to 20% by weight, based on the overall weight of the composition. The salt is employed in an amount which is effective for improving the ease of washing out the polymers. The salt is generally employed in a quantity of 0.02 to 10% by weight, preferably 0.1 to 8% by weight, based on the overall weight of the composition.

The weight ratio of component (A) to component (B) is generally in the range from 1:0.01 to 1:1.0, preferably from 1:0.02 to 1:0.5.

The salts employed in accordance with the invention improve both the ease of washing out of the hairsetting polymers and their film characteristics. They endow the hair treated with the compositions according to the invention with brilliance and smoothness and decrease the stickiness of the hairsetting polymers. Moreover, the carboxylic acids of the invention are useful as additives in cosmetics, pharmacy, and textile and paper industries, especially as solubilizers, tensides, emulsifiers or protective colloids and for the improvement of the surface properties of films to which they give smoothness and brilliance. This especially applies to the siloxane-containing acids and bases respectively. By using them, hair treatment compositions can be formulated with up to 0.2% by weight, based on the overall weight of the composition, of a silicone. The resulting films are smooth, clear and readily to be washed out.

The novel hair treatment compositions are usually in the form of an aqueous dispersion or of an aqueous alcoholic solution. Examples of suitable alcohols are ethanol, propanol, isopropanol, etc.

Furthermore, the novel hair treatment compositions generally include customary cosmetic auxiliaries, examples being plasticizers, such as glycerol and glycol; silicones; emollients, lubricants and penetrating agents, such as lanolin compounds; fragrances; UV absorbers; colorants; thickeners; antistatic agents; combability improvers; preservatives; and foam stabilizers. The compositions may also include at least one other hairsetting polymer.

If the novel compositions are formulated as a hairspray, they include a sufficient quantity of a propellant, for example a low boiling hydrocarbon or ether, such as propane, butane, isobutane or dimethyl ether. Compressed gases can also be used as propellants, examples being nitrogen, air or carbon dioxide. The amount of propellant is kept as low as possible in order not unnecessarily to increase the VOC content. In general it is not more than 40% by weight, based on the overall weight of the composition.

The novel compositions possess the advantage that on the one hand they give the hair the desired set and on the other hand the polymers present in the compositions are relatively easy to wash out (redispersible). Moreover, it is possible to produce formulations having a VOC content of less than 60% and even purely aqueous formulations, even when they are formulated as a hairspray.

The examples which follow illustrate the invention:

EXAMPLE 1
Polyurethane Preparation:

0.5 mol of polyesterdiol ($M_w$=1000 g/mol) prepared from isophthalic acid, adipic acid and hexanediol, 0.6 mol of diethylene glycol and 1.25 mol of dimethylolpropanoic acid were dissolved with heating at 80° C. and with stirring in methyl ethyl ketone (about 50% strength solution) in a four necked flask which was fitted with stirrer, dropping funnel, thermometer, reflux condenser and a device for operating under nitrogen. As soon as all the components had dissolved, the reaction mixture was cooled to about 500C. Then 2.5 mol of isophorone diisocyanate were added dropwise with stirring, and the reaction temperature rose. The reaction mixture was then stirred at reflux temperature until the isocyanate group content of the mixture remained virtually constant. The residual isocyanate groups were deactivated by adding an amine, for example 2-amino-2-methyl-1-propanol. Free COOH groups were neutralized with 2-amino-2-methylpropanol. Then water was added and the major portion of the methyl ethyl ketone was removed under reduced pressure at about 40° C., to give a dispersion of the polyurethane which was used for the tests described in Example 2 below.

EXAMPLE 2
Ease of Washing Out the Polymers:

The ease of washing out the polymer obtained in accordance with Example 1 was investigated. For this purpose, a film of the polymer was produced on a glass plate by pouring the polymer dispersion onto the glass plate. The film was left to dry at room temperature for 20 h. The ease of washing out (redispersibility) with water or water/ethanol (1:1 v/v) was determined by rubbing with a finger. In test 1 no salt was added, while in tests 2 to 4 5% by weight of the polymer was replaced by one of the following salts:

A. salt of 1 mol of isophthalic acid and 2 mol of 2 amino 2 methylpropanol;

B. salt of 1 mol of 5-$NaSO_3$-isophthalic acid and 2 mol of 2-amino-2-methylpropanol;

C. salt of 1 mol of 1,3,5-benzenetricarboxylic acid and 3 mol of 2-amino-2-methylpropanol.

The results obtained are shown in the table below.

TABLE

| | | | Ease of washing out the polymers | |
|---|---|---|---|---|
| | | | | Ease of washing out with |
| Test | K value of the polyurethane | Salt | film produced from aqueous dispersion | film produced from $H_2O$:EtOH dispersion |
| 1 | 27 | — | poor | poor |
| 2 | 27 | A | good | good |
| 3 | 27 | B | good | good |
| 4 | 27 | C | good | good |

It is evident that the films obtained with the novel compositions are, surprisingly, easier to wash out than the film obtained with the prior art composition.

EXAMPLE 3

Hairspray Formulations with a VOC Content of 55% by Weight:

| | Formulation | |
|---|---|---|
| | with salt | without salt |
| Polyurethane of Example 1 | 4.75% by wt. | 5% by wt. |
| Water | 40% by wt. | 40% by wt. |
| Ethanol | 25% by wt. | 25% by wt. |
| Dimethyl ether | 30% by wt. | 30% by wt. |
| Salt A, B or C | 0.25% by wt. | — |
| Fragrance q.s. | | |

The ease of Washing out the films obtained with these formulations was determined on artificial model heads as follows:

The hairspray was applied to the hair of the model heads in one spraying lasting 10 seconds (quantity applied about 2.5 g). After drying for two hours in a controlled climate chamber (atmospheric humidity 45%; temperature 20° C.) the setting effect was assessed. This procedure was repeated 3 times in all. The sprayed model head was dried overnight in the controlled climate chamber. The hair was then shampooed with Texapon NSO for no more than 5 minutes and washed. After drying, the ease of washing out was assessed by trained experts. It was found that the film obtained with the novel composition (formulation with salt) was easy to wash out, whereas the film obtained with the no salt composition could washed out only with difficulty.

EXAMPLE 4 a) Preparation of a salt of a carboxylic acid of formula VII (if n1+n2=0)

93 g (0.1 mol) of Tego OF 2010 (polydimethylsiloxane diamine of Goldschmidt Co.) and 26 g (0.2 mol) of itaconic acid in 45 g ethanol:water (1:1) were stirred at reflux temperature for 2 hours. After distilling off the ethanol and the water, the temperature of the reaction mixture was maintained at 140–170° C. for another 2 hours. A yellow, viscous substance was obtained which was readily soluble in ethanol and which formed a stable dispersion after neutralisation with 2 moles of 2-amino-2-methylpropanol in water.

b) Preparation of a salt of a carboxylic acid of formula VII (if $R^5$=—$CH_2$—$CH_2$—; n1+n2=5)

1 mol of Tego OF 2010 and 7 mol of itaconic acid in 450 g ethanol:water (1:1) were stirred at reflux under nitrogen for 2 hours. After distilling off the ethanol and the water, the temperature of the reaction mixture was maintained at 140–170° C. for another 2 hours. Afterwards, 5 mol of ethylenediamine in water (1:1) were added and the above treatment was repeated. A solid yellow product was obtained which was readily soluble in ethanol and which after neutralisation formed a stable dispersion with 2-amino-2-methylpropanol in water.

EXAMPLE 5

Preparation of a Carboxylic Acid Salt of Formula VIII:

83 g (0.1 mol) of Tego OF 2010 (polydimethylsiloxane diamine of Goldschmidt Co.) and 29 g (0,09 mol) of 3,3', 4,4'-benzophenone-tetracarboxylic acid dianhydride (BPDA) in 50 g ethanol:water (1:1) were stirred at room temperature for approximately 1 hour. The temperature of the reaction mixture was then maintained at about 40–70° C. for 3 hours while stirring. Neutralisation with aminoethylpropanol yielded a clear yellow solution which resulted after drying at 120° C./vacuum in an elastic product. The product was soluble in ethanol and formed a very stable aqueous dispersion.

EXAMPLE 6

Preparation of a Salt of a Monobasic Carboxylic Acid and a Bivalent Amine 93 g (0.1 mol) of Tegomer A-Si 2120 (polydimethylsiloxane diamine, about 930) was neutralised with 20 g 90% lactic acid (0.2 mol). The resulting salt was dissolved in 330 g of ethanol. 0.44 g Abil 200 (polydimethylsiloxane of Goldschmidt Co.) was added. An almost clear, stable dispersion was obtained.

EXAMPLE 7

The characteristics of a polymer film were determined, said polymer film being formed out of ethanol/$H_2O$ (8/2 v/v). The ease of washing out was determined according to example 2. Transparency was determined visually, and the smoothness of the film was determined by experienced examiners by rubbing with fingers over the film. In experiments 1, 2, 7 and 8, no salt was added, in experiments 3 to 6, 9 and 10, part of the polymer was replaced by the salts produced in examples 4 to 6. In experiments 2 and 5 to 10, 0.0005 or 0.001% by weight of silicone oil were also added to the dispersion. The resuits are shown in the following table 2.

TABLE 2

Characteristics of the resulting polymer films

| Experiment No. | Polymer % by weight[4] | Salt Example | Salt % by weight | silicon oil % by weight | film characteristics smoothness | film characteristics transparency | ease of washing out |
|---|---|---|---|---|---|---|---|
| 1 | 5[4] | — | — | — | fairly smooth | clear | bad |
| 2 | 5[4] | — | — | 0.0005 | smooth | turbid | bad |
| 3 | 3[4] | 4a | 2 | — | smooth | clear | good |
| 4 | 3[4] | 5 | 2 | — | smooth | clear | good |
| 5 | 3[4] | 5 | 2 | 0.001 | very smooth | clear | good |
| 6 | 4.5[4] | 6[1] | 0.5 | 0.002 | very smooth | clear | leachable |
| 7 | 5[2] | — | — | 0.0005 | smooth | slightly turbid | bad |
| 8 | 5[3] | — | — | 0.0005 | smooth | slightly turbid | leachable |
| 9 | 4.5[2] | 6[1] | 0.5 | 0.002 | very smooth | clear | leachable |
| 10 | 4.5[3] | 6 | 0.5 | 0.002 | very smooth | clear | leachable |

*)Polyurethane according to example 1 was used for experiments 1 to 6
[1]The formulation was produced of 4.5 g of polymer neutralised with AMP and 2 g of the solution according to example 6 (corresponds to 0.5 g salt + 0.002 g of silicone oil in 1.5 g ethanol). Then this was dissolved with 20 g of water and 78 g of ethanol.
[2]Luvimer ® 100P: terpolymer of t-butyl acrylate, ethyl acrylate and methacrylic acid (BASF)
[3]Luviskol ® Plus*: polyvinylcaprolactam (BASF)
[4]Polymer according to example 1
AMP = 2-amino-2-methyl-1-propanol

We claim:

1. A hair treatment composition comprising:
   i) at least one water soluble or dispersible hairsetting polymer (A) selected from the group consisting of polyurethanes, polyesters, polyamides, poly(amide) esters, and homopolymers and copolymers of monoolefinically unsaturated monomers, wherein these polymers have ionogenic and/or ionic groups attached to the polymer chain, and
   ii) a water soluble or dispersible (poly)siloxane-containing salt (B) of the formula I $[A(X)_n]^{n-} \cdot (n/m)[H_mB]^{m+}$ (I)

wherein $[A(X)_n]^{n-}$ is the anion of a siloxane-containing acid, where
X is a carboxylate or sulfonate group, and
n is the valency of the (poly)siloxane-containing acid;

B is a cosmetically acceptable amine base;
m is the valency of the amine B;

wherein the weight ratio of the hairsetting polymer (A) to the (poly)siloxane-containing salt (B) is from 1:0.01 to 1:0.5, and wherein the (poly)siloxane-containing acid is selected from a) polycondensates which in addition to polysiloxane moieties comprise moieties selected from the group consisting of polyurethane and polyurea moieties, the polyurethane moieties and polyurea moieties comprising carboxylic and/or sulfonic groups, (b) dibasic acids of the formula (VII)

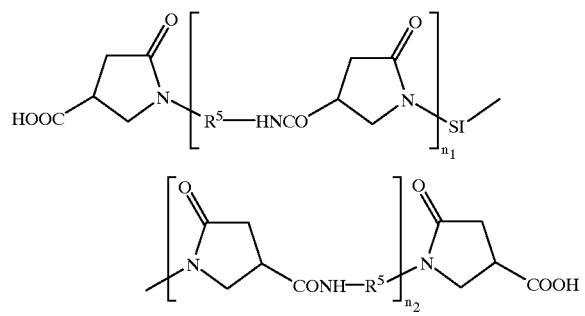

(VII)

wherein $R^5$ is $C_2$–$C_4$ alkylene,
$n_1+n_2$ is 0 to 20, and

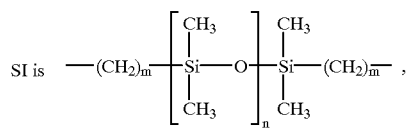

where m is 1 to 6 and n is 1 to 50, and (c) siloxane-containing, polybasic acids of the formula (VIII)

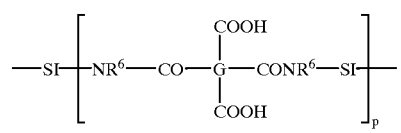

(VIII)

wherein $R^6$ is H or $C_1$–$C_6$ alkyl,
p is 1 to 100, and

G is the tetravalent rest of a dianhydride of the formula

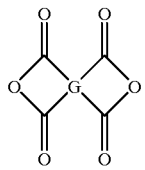

selected from the group consisting of

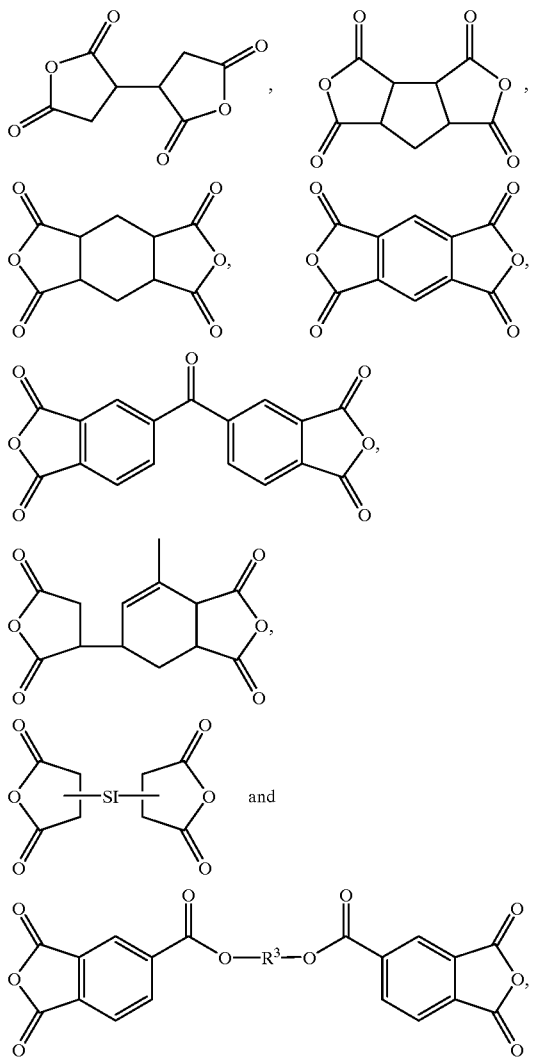

wherein $R^3$ is $C_1$–$C_6$ alkylene.

2. The composition of claim 1, further comprising a water-insoluble silicone.

3. The composition of claim 1, further comprising dimethicon.

4. The composition of claim 2 comprising
i) a siloxane-free-hairsetting polymer,
ii) a (poly)siloxane-containing salt $[A(X)_n]^{n-} \cdot (n/m)[H_mB]^{m+}$, and
iii) a water-insoluble silicone.

5. The composition of claim 4 consisting of
i) 0.5 to 15% by weight of a siloxane-free hair setting polymer, ii) 0.1 to 8% by weight of the salt $[A(X)_n]^{n-} \cdot (n/m)[H_mB]^{m+}$, and iii) 0.005 to 0.15% by weight of water-insoluble silicone.

6. The composition of claim 4 consisting of
    i) 0.5 to 15% by weight of a siloxane-free hair setting polymer,
    ii) 0.1 to 8% by weight of the salt $[A(X)_n]^{n-} \cdot (n/m)[H_mB]^{m+}$, and
    iii) 0.001 to 0.1% by weight of water-insoluble silicone.

7. The composition of claim 1, wherein the amine base is selected from the group consisting of di-$C_1$–$C_6$-alkyl-ethanolamines, mono-$C_1$–$C_6$-alkyl-diethanolamines, monoethanolamine, diethanolamine, triethanolamine, 2-amino-2-methylpropanol and 2-amino-2-methylolpropanol, N-methlyldipropylenetriamine and N-methylglucamine.

8. A hair treatment composition comprising:
    i) at least one water soluble or dispersible hair setting polymer (A) selected from the group consisting of polyurethanes, polyesters, polyamides, poly(amide) esters, and homopolymers and copolymers of monoolefinically unsaturated monomers, wherein these polymers have ionogenic groups attached to the polymer chain,
    ii) a water soluble or dispersible (poly)siloxane-containing salt (B) of the formula I $$[A(X)_n]^{n-} \cdot (n/m)[H_mB]^{m+} \qquad (I)$$

wherein
A is a cosmetically acceptable, aliphatic, cycloaliphatic or aromatic radical which is unsubstituted or carries 1, 2 or 3 substituents selected from the group consisting of $C_1$–$C_6$ alkyl, $C_1$–$C_6$ alkoxy, mono- and polyhydroxy $C_1$–$C_6$ alkyl, hydroxyl and amino, it being possible for the chain of the aliphatic radical to be interrupted by up to 30-CONH— groups and for the ring of the cycloaliphatic radical to have a —CO—N group, with two cycloaliphatic radicals being attached in each case to the nitrogen atom by way of a $C_2$–$C_6$ alkylene or p-xylene group;

X is a carboxylate, or sulfonate group;

n is 1 to 30; and $[H_mB]^{m+}$ is the cation of a (poly)siloxane-containing amine B and m is the valency of the amine B;

wherein the weight ratio of hairsetting polymer (A) to (poly)siloxane-containing salt (B) is from 1:0.01 to 1:0.5, and wherein the (poly)siloxane-containing polyvalent amine is a polycondensate which, in addition to polysiloxane moieties, comprises moieties selected from the group consisting of polyurethane and polyurea moieties, the polyurethane and polyurea moieties comprising amino groups.

9. The composition of claim 8, further comprising a water-insoluble silicone.

10. The composition of claim 8, further comprising a dimethicon.

11. The composition of claim 9 comprising
    i) a siloxane-free hairsetting polymer,
    ii) a (poly)siloxane-containing salt $[A(X)_n]^{n-} \cdot (n/m)[H_mB]^{m+}$, and
    iii) a water-insoluble silicone.

12. The composition of claim 11 consisting of
    i) 0.5 to 15% by weight of a siloxane-free hair setting polymer, ii) 0.1 to 8% by weight of the salt $[A(X)_n]^{n-} \cdot (n/m)[H_mB]^{m+}$, and iii) 0.005 to 0.15% by weight of water-insoluble silicone.

13. The composition of claim 11 consisting of
    i) 0.5 to 15% by weight of a siloxane-free hair setting polymer,
    ii) 0.1 to 8% by weight of the salt $[A(X)_n]^{n-} \cdot (n/m)[H_mB]^{m+}$, and
    iii) 0.001 to 0.1% by weight of water-insoluble silicone.

14. The composition of claim 8, wherein the salt is formed from the polysiloxane-containing amine B and at least one carboxylic acid which is selected from the group consisting of aromatic polycarboxylic acids having 1 to 4 carboxyl groups, which may contain 1 to 3 radicals selected from hydroxyl and sodium sulfonate, aliphatic carboxylic acids having 1 to 12 carbon atoms, which carry 1 to 6 carboxyl groups and which may contain up to 6 hydroxyl groups, cycloaliphatic acids, having 1 to 4 carboxyl groups, which may contain 1 or 2 hydroxyl groups, monobasic acids of the formulae IV or V

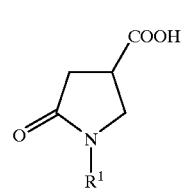

(V)

wherein $R^1$ is a group

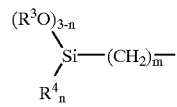

where n is 0 to 3, m is 1 to 6 and $R^3$ and $R^4$ are $C_1$–$C_6$ alkyl, $R^2$ is a group —$(CH_2)_m$— where m is 2 to 6,

, 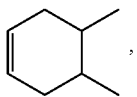

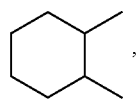, 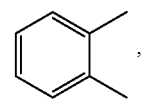

dibasic acids of the formula (VII)

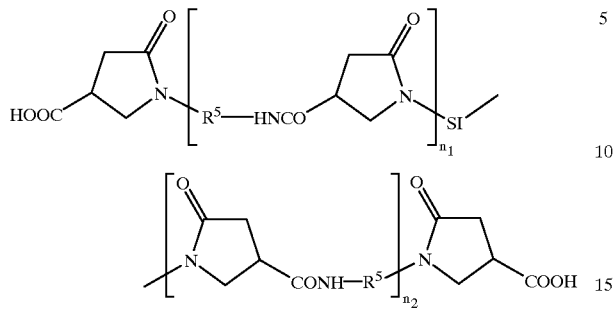

wherein

R⁵ is $C_2$–$C_4$ alkylene, $n_1+n_2$ is 0 to 20, and

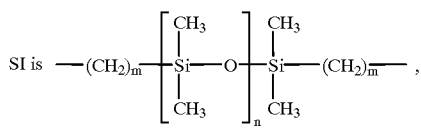

where m is 1 to 6 and n is 1 to 50, and siloxane-containing, polybasic acids of the formula (VIII)

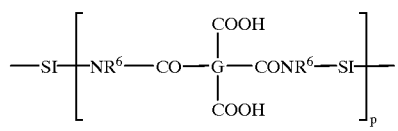

wherein

R⁶ is H or $C_1$–$C_6$ alkyl p is 1 to 100, and

G is the tetravalent rest of a dianhydride of the formula

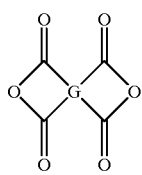

selected from the group consisting of

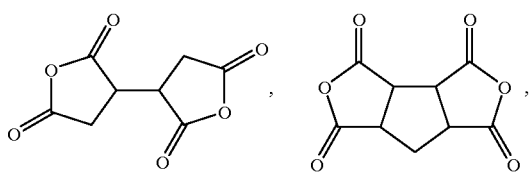

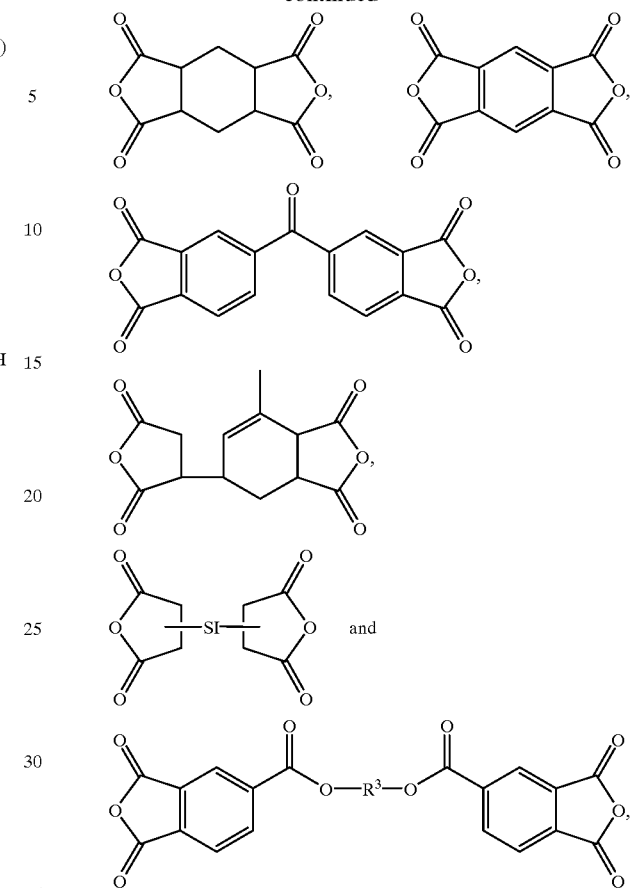

wherein R³ is $C_1$–$C_6$ alkylene.

15. The composition of claim 1 wherein the (poly) siloxane-containing acid is selected from polycondensates (a) with polysiloxane moieties of the formula

 (IX)

and with polyurethane and/or poyurea moieties of the formula

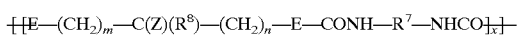

wherein

E is O or NH and

R⁷ is $C_1$–$C_6$ alkylene or phenylene

R⁸ is H or $C_1$–$C_4$ alkyl,

Z is COOH of $SO_3H$, m and n independently are 1 to 6 and x is 1 to 10.

16. The composition of claim 8 wherein the (poly) siloxane-containing polyvalent amine is selected from polycondensates with polysiloxane moieties of the formula

 (IX)

and with polyurethane and/or poyurea moieties of the formula

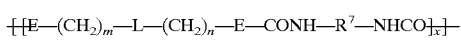

wherein
E is O or NH,
L is —C(Z)(R$^8$)— or —N(R$^8$)—,
R$^7$ is C$_1$–C$_4$ alkyl,
Z is NR$^{11}$R$^{12}$, m and n are independently 1 to 6,
x is 1 to 10 and
R$^{11}$ and R$^{12}$ are independently C$_1$–C$_6$ alkyl.

* * * * *

UNITED STATES PATENT AND TRADEMARK OFFICE
CERTIFICATE OF CORRECTION

PATENT NO.   : 6,368,583 B1
DATED        : April 9, 2002
INVENTOR(S)  : Kim et al.

It is certified that error appears in the above-identified patent and that said Letters Patent is hereby corrected as shown below:

Column 22,
Line 28, insert the following:
-- $R_1$-NHOO-$R^2$-COOH    (IV) --.

Signed and Sealed this

Eighth Day of October, 2002

JAMES E. ROGAN
Director of the United States Patent and Trademark Office

UNITED STATES PATENT AND TRADEMARK OFFICE
CERTIFICATE OF CORRECTION

PATENT NO. : 6,368,583 B1
DATED : April 9, 2002
INVENTOR(S) : Kim et al.

It is certified that error appears in the above-identified patent and that said Letters Patent is hereby corrected as shown below:

<u>Column 22,</u>
Line 28, insert the following:
-- $R^1$-NHCO-$R^2$-COOH --.

This certificate supersedes Certificate of Correction issued October 8, 2002.

Signed and Sealed this

Thirteenth Day of May, 2003

JAMES E. ROGAN
*Director of the United States Patent and Trademark Office*